(12) United States Patent
Budge

(10) Patent No.: US 10,898,338 B1
(45) Date of Patent: Jan. 26, 2021

(54) REVERSE SHOULDER PROSTHESIS

(71) Applicant: Matthew Budge, Tualatin, OR (US)

(72) Inventor: Matthew Budge, Tualatin, OR (US)

(*) Notice: Subject to any disclaimer, the term of this patent is extended or adjusted under 35 U.S.C. 154(b) by 100 days.

(21) Appl. No.: 16/215,136

(22) Filed: Dec. 10, 2018

Related U.S. Application Data

(60) Provisional application No. 62/618,243, filed on Jan. 17, 2018.

(51) Int. Cl.
*A61F 2/40* (2006.01)
*A61F 2/30* (2006.01)

(52) U.S. Cl.
CPC .......... *A61F 2/4014* (2013.01); *A61F 2/4059* (2013.01); *A61F 2/4081* (2013.01); *A61F 2002/30604* (2013.01); *A61F 2002/30878* (2013.01); *A61F 2002/4022* (2013.01); *A61F 2002/4029* (2013.01); *A61F 2002/4044* (2013.01); *A61F 2002/4085* (2013.01); *A61F 2220/0025* (2013.01)

(58) Field of Classification Search
CPC .......... A61F 2/4014; A61F 2002/4044; A61F 2/389; A61F 2/3868; A61F 2/3872
See application file for complete search history.

(56) References Cited

U.S. PATENT DOCUMENTS

| | | | | |
|---|---|---|---|---|
| 5,755,801 A | * | 5/1998 | Walker | A61F 2/3868 623/20.21 |
| 5,871,545 A | * | 2/1999 | Goodfellow | A61F 2/3868 623/20.28 |
| 6,162,254 A | * | 12/2000 | Timoteo | A61F 2/3868 623/20.27 |
| 6,228,120 B1 | * | 5/2001 | Leonard | A61F 2/4684 623/19.12 |
| 8,702,800 B2 | | 4/2014 | Linares et al. | |
| 9,498,344 B2 | | 11/2016 | Hodorek et al. | |
| 2001/0014827 A1 | * | 8/2001 | Chambat | A61F 2/3868 623/20.33 |
| 2003/0028253 A1 | * | 2/2003 | Stone | A61F 2/4014 623/19.14 |
| 2005/0209702 A1 | * | 9/2005 | Todd | A61F 2/3868 623/20.33 |
| 2006/0020344 A1 | * | 1/2006 | Shultz | A61F 2/40 623/19.12 |

(Continued)

*Primary Examiner* — Bruce E Snow
*Assistant Examiner* — Melissa A Hoban
(74) *Attorney, Agent, or Firm* — Klarquist Sparkman, LLP

(57) ABSTRACT

Embodiments of an implant assembly for reverse shoulder arthroplasty is disclosed. In one embodiment, the implant assembly comprises a humeral component and an adaptor coupled to the humeral component. The humeral component comprises a stem portion and a neck portion. The stem portion is configured for fixation to a humerus, and the neck portion is angularly oriented relative to the stem portion. The adaptor comprises a first bearing surface and a second bearing surface opposite the first bearing surface. The first bearing surface interfaces with an articulating surface of the neck portion to allow the adaptor to rotate relative to the humeral component in a plane that is generally parallel to the articulating of the neck portion. The second bearing surface is configured to interface with a glenosphere component to allow the glenosphere component to articulate relative to the adaptor.

20 Claims, 11 Drawing Sheets

(56) References Cited

U.S. PATENT DOCUMENTS

| | | | |
|---|---|---|---|
| 2006/0195195 A1* | 8/2006 | Burstein | A61F 2/3868 623/20.33 |
| 2009/0171462 A1* | 7/2009 | Poncet | A61F 2/4014 623/19.12 |
| 2009/0192621 A1* | 7/2009 | Winslow | A61F 2/40 623/19.14 |
| 2009/0216332 A1* | 8/2009 | Splieth | A61F 2/4684 623/19.14 |
| 2011/0054624 A1* | 3/2011 | Iannotti | C12N 15/86 623/19.14 |
| 2011/0106267 A1* | 5/2011 | Grant | A61F 2/4014 623/19.14 |
| 2011/0118846 A1* | 5/2011 | Katrana | A61F 2/4014 623/19.13 |
| 2011/0295377 A1* | 12/2011 | Dees, Jr. | A61F 2/3868 623/20.32 |
| 2012/0078375 A1* | 3/2012 | Smith | A61F 2/4014 623/20.35 |
| 2012/0209392 A1 | 8/2012 | Angibaud et al. | |
| 2013/0204375 A1* | 8/2013 | Winslow | A61F 2/4014 623/19.13 |
| 2013/0325131 A1 | 12/2013 | Roche et al. | |
| 2014/0236304 A1* | 8/2014 | Hodorek | A61B 17/164 623/19.14 |
| 2014/0288657 A1* | 9/2014 | Lederman | A61F 2/4014 623/19.14 |
| 2015/0039093 A1* | 2/2015 | McTighe | A61F 2/4014 623/23.14 |
| 2015/0265411 A1* | 9/2015 | Deransart | A61F 2/4014 623/19.14 |
| 2016/0030187 A1* | 2/2016 | Sperling | A61F 2/4014 623/19.14 |
| 2016/0051368 A1 | 2/2016 | Wiley et al. | |
| 2016/0262902 A1 | 9/2016 | Winslow et al. | |

* cited by examiner

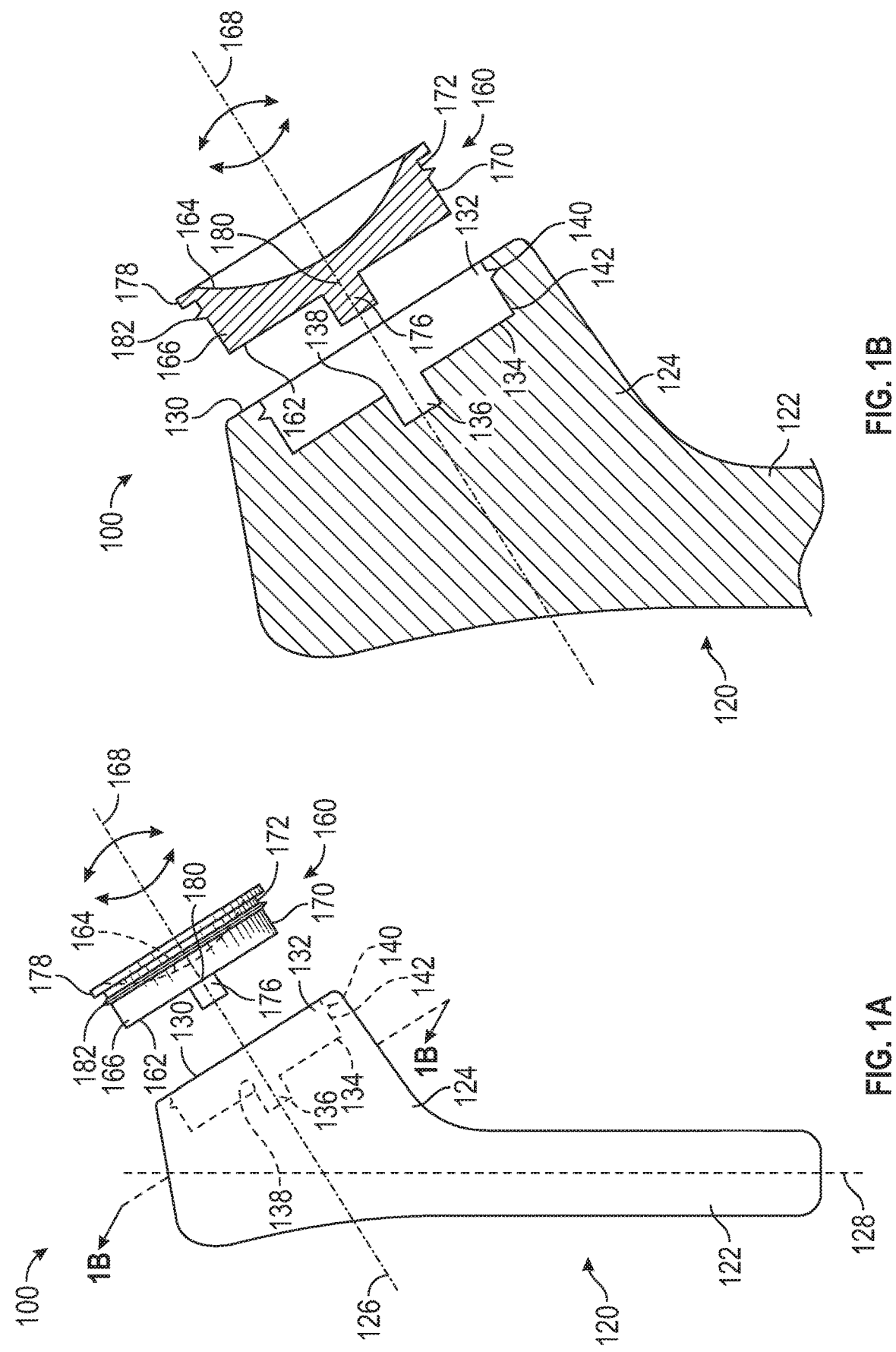

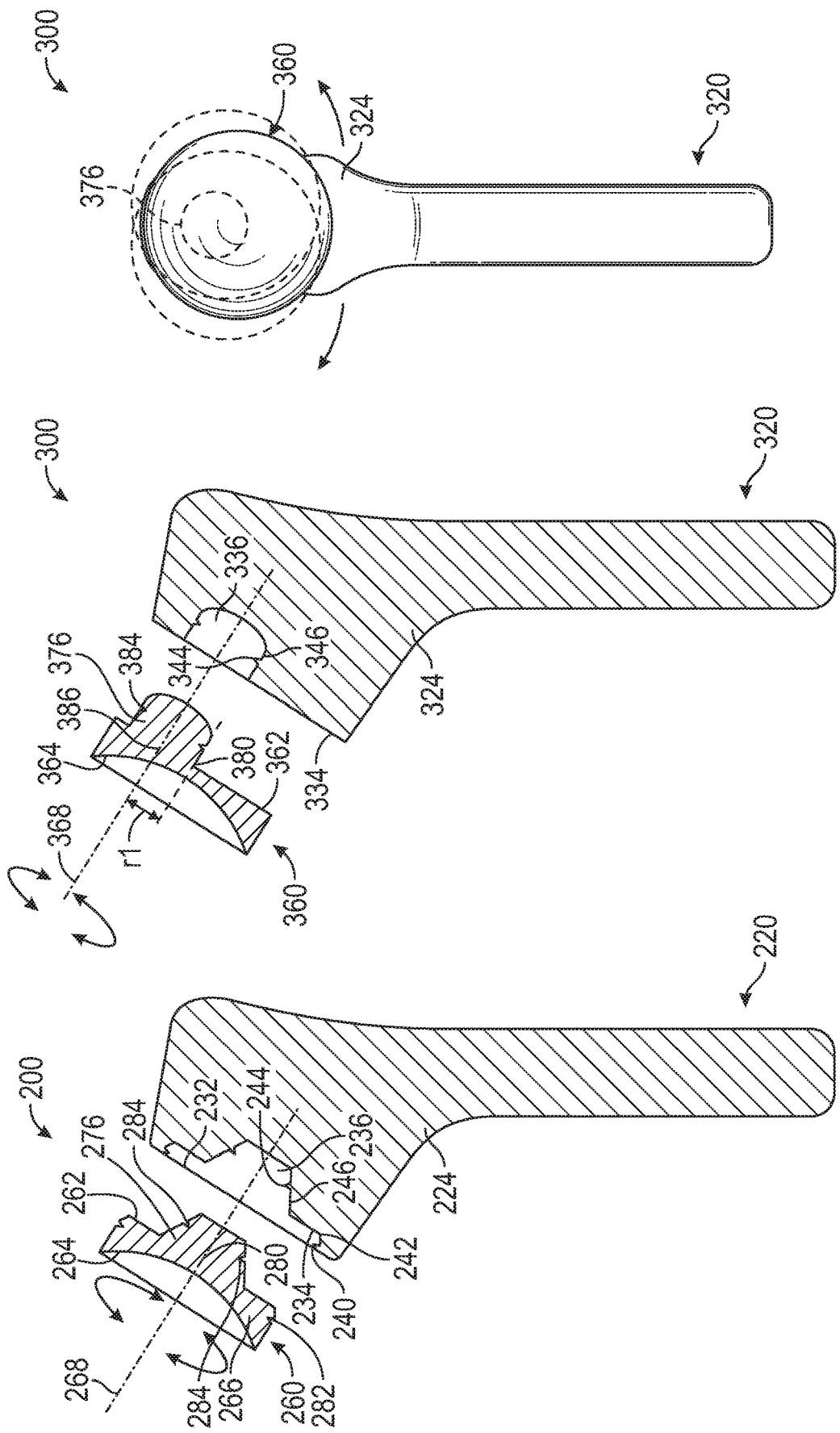

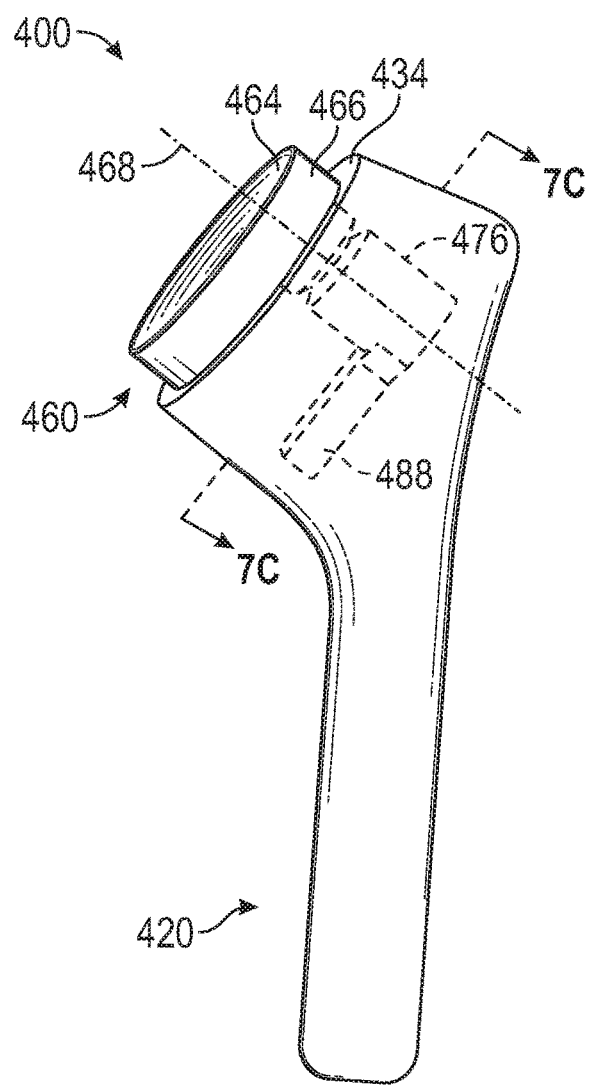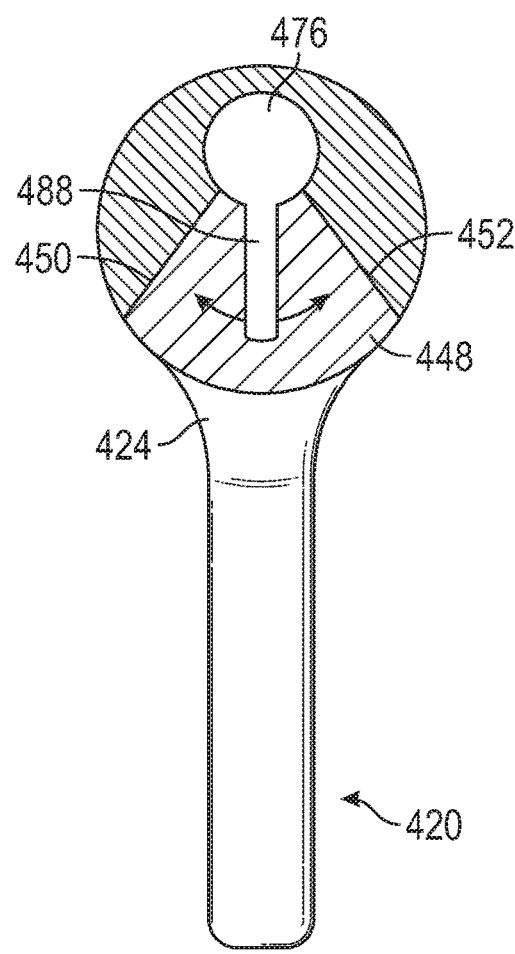
FIG. 7B
FIG. 7C

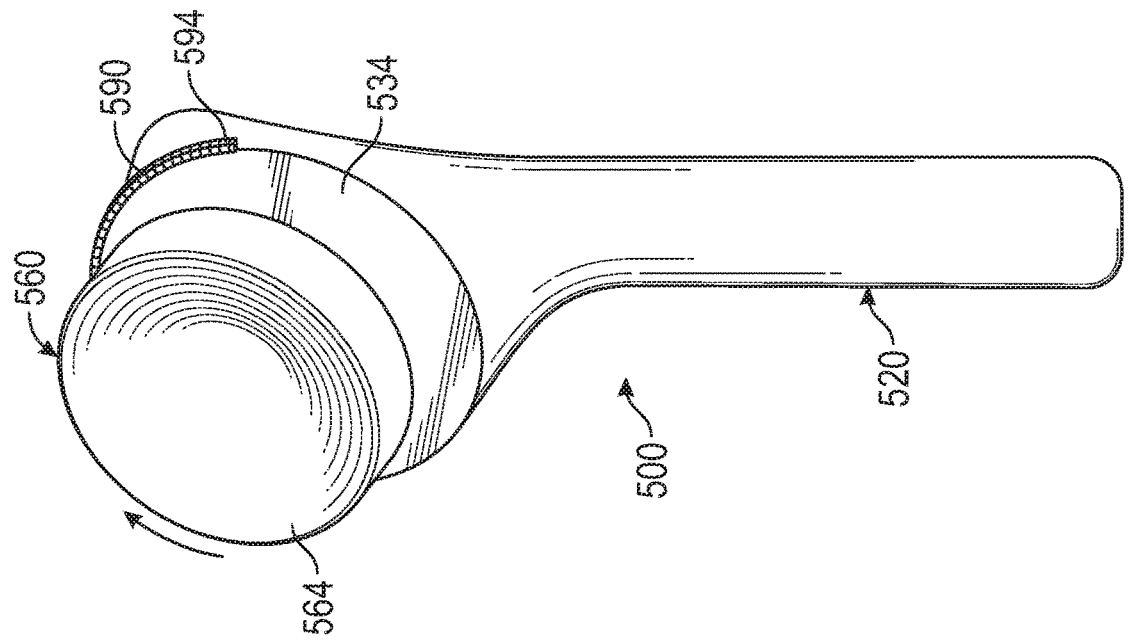
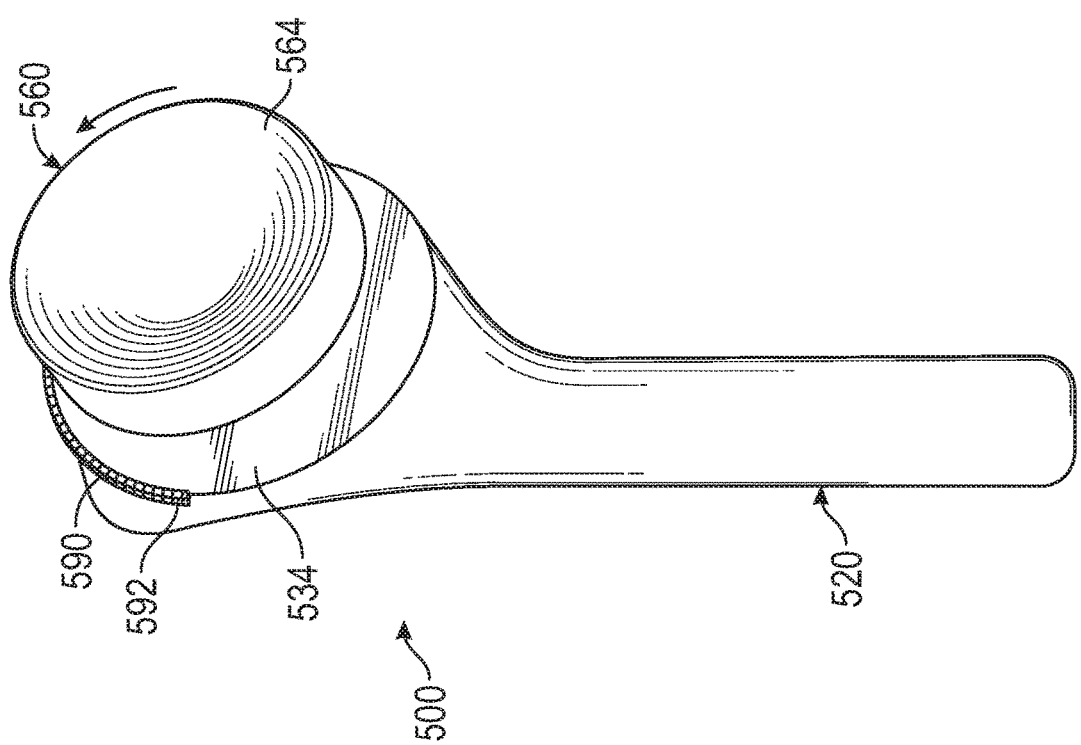

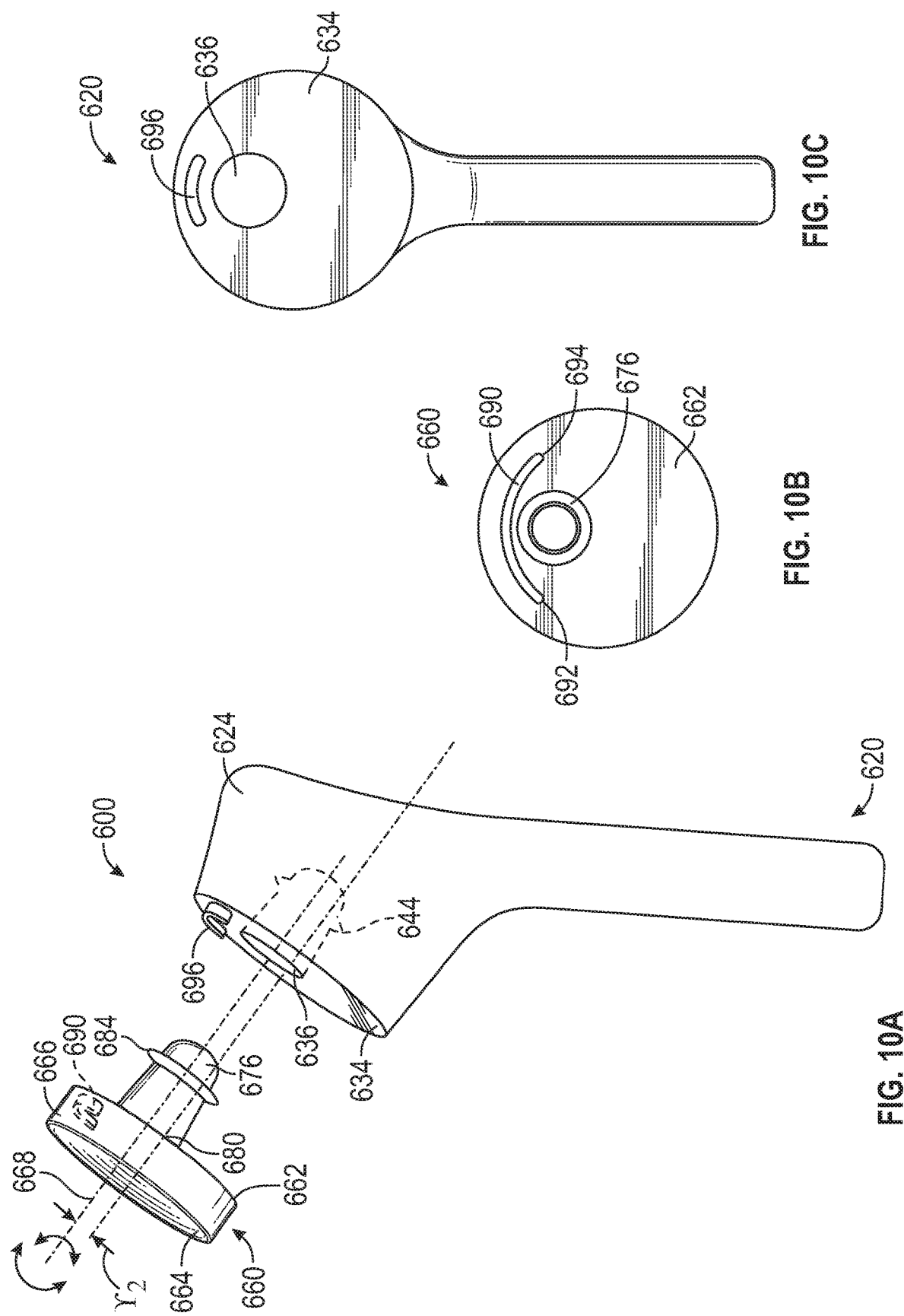

REVERSE SHOULDER PROSTHESIS

CROSS-REFERENCE TO RELATED APPLICATIONS

This application claims the benefit of U.S. Provisional Application Ser. No. 62/618,243, filed Jan. 17, 2018, which is incorporated by reference herein.

FIELD

The present disclosure concerns embodiments of an implant assembly for joint replacement surgery, such as shoulder arthroplasty.

BACKGROUND

Shoulder arthroplasty is a treatment for some people with shoulder pain from arthritis. When standard shoulder arthroplasty is performed, a cup is placed in the shoulder socket and a ball is placed at the upper end of the humerus to mimic the normal anatomic shoulder. However, patients who do not have enough muscle function to stabilize the joint may not be able to benefit from the standard shoulder arthroplasty. To overcome such a problem, a reverse shoulder arthroplasty can be performed by switching the positions of the components, that is, the ball is placed in the socket and the cup is placed at the upper end of the humerus.

One of the unsolved problems in the field of reverse shoulder arthroplasty is the maintenance of internal and external rotation of the humerus when placing a reverse total shoulder arthroplasty. The non-anatomic nature of the reverse total shoulder arthroplasty can prevent full return of internal and external rotation through a variety of mechanisms including impingement on bone or soft tissue, lack of adequate muscle strength, and limitations of the rotational surface area of the bearing surface. Accordingly, it is desirable to further improve the reverse shoulder arthroplasty so as to allow the humerus to achieve full rotation even in the setting of bone/soft tissue impingement or limited rotation surface area.

SUMMARY

The present disclosure is directed toward methods and apparatuses relating to joint replacement surgery, specifically relating to reverse shoulder arthroplasty.

Certain embodiments of the disclosure concern an implant assembly including a humeral component and an adaptor coupled to the humeral component. The humeral component can have a stem portion and a neck portion. The stem portion can be configured for fixation to a humerus. The neck portion can be angularly oriented relative to the stem portion. The adaptor can have a first bearing surface and a second bearing surface opposite the first bearing surface. The first bearing surface of the adaptor can interface with an articulating surface of the neck portion to allow the humeral component to rotate relative to the adaptor in a plane that is generally parallel to the first bearing surface of the adaptor. The second bearing surface of the adaptor can be configured to interface with a glenosphere component to allow the glenosphere component to articulate relative to the adaptor.

In some embodiments, the adaptor can include a first coupling member matingly engaged with a second coupling member of the neck portion.

In some embodiments, the first coupling member can include a shaft extending from the first bearing surface, and the second coupling member can include a recess in the neck portion configured to receive the shaft.

In some embodiments, the first coupling member can be aligned with a rotational axis of the adaptor.

In some embodiments, the rotational axis can pass through a geometric center of the first bearing surface.

In some embodiments, a geometric center of the first bearing surface can have a radial offset relative to the rotational axis.

In some embodiments, the implant assembly can further include a locking mechanism configured to prevent the adaptor from decoupling from the humeral component.

In some embodiments, the locking mechanism can include a tongue-and-groove joint between the adaptor and the humeral component so as to allow rotational movement of the humeral component relative to the adaptor but resist displacement of the adaptor from the plane of rotation.

In some embodiments, the first coupling member can include a shank member extending outwardly from the first bearing surface and a keel member angularly extending from the shank member.

In some embodiments, the second coupling member can include a channel and a chamber connected to the channel. In some embodiments, the shank can be positioned in the channel and the keel can be angularly moveable within the chamber.

In some embodiments, the chamber can have a first angular boundary and a second angular boundary, and the angular movement of the keel within the chamber can be limited by the first and second angular boundaries.

In some embodiments, the first angular boundary and the second angular boundary can define a circular sector having an angle from about 30° to about 150°.

In some embodiments, the implant assembly can further include a first limiter and a second limiter disposed on a proximal surface of the neck portion. In some embodiments, the first and second limiters can be configured to limit rotational movement of the humeral component relative to the adaptor.

In some embodiments, the first limiter can be angularly spaced apart from the second limiter from about 30° to about 150°.

In some embodiments, the first and second limiters can be connected by a curved ring.

In some embodiments, the implant assembly can further include the glenosphere component. The glenosphere component can include a base configured for fixation to a glenoid fossa of scapula and a convex surface that articulates against the second bearing surface of the adaptor. In some embodiments, the second bearing surface of the adaptor can be concave.

In some embodiments, the first bearing surface of the adaptor can be planar.

In some embodiments, the first bearing surface of the adaptor can be curved.

In some embodiments, the second coupling member can be a shaft extending outwardly relative to the bearing surface of the neck portion, and the first coupling member can be a recess in the adaptor configured to receive the shaft.

Certain embodiments of the disclosure concern also concern an implant assembly including a humeral component having a stem portion and a neck portion proximal to the stem portion. The stem portion can be configured for fixation to a humerus, and the neck portion can be angularly oriented relative to the stem portion. The implant assembly can also include an adaptor rotatably coupled to the neck portion of the humeral component around a rotational axis. The rotational axis can form a fixed angle relative to the stem portion of the humeral component.

In some embodiments, the implant assembly can further include a glenosphere component, which can include a base configured for fixation to a glenoid fossa of scapula and a convex surface that articulates against a concave bearing surface of the adaptor.

In some embodiments, the adaptor can include a first coupling member matingly engaged with a second coupling member of the neck portion. The rotational axis can pass through the first and second coupling members.

In some embodiments, the first coupling member can include a shaft extending from a distal bearing surface, and the second coupling member can include a recess in the neck portion configured to receive the shaft.

In some embodiments, the rotational axis can pass through a geometric center of the distal bearing surface.

In some embodiments, a geometric center of the distal bearing surface can have a radial offset relative to the rotational axis.

In some embodiments, the implant assembly can further include a locking mechanism configured to prevent the adaptor from decoupling from the humeral component.

In some embodiments, the locking mechanism can include a tongue-and-groove joint between the adaptor and the humeral component so as to allow rotational movement of the humeral component relative to the adaptor but resist displacement of the adaptor along the rotational axis.

In some embodiments, the first coupling member can include a shank member extending outwardly from the distal bearing surface and a keel member angularly extending from the shank member.

In some embodiments, the second coupling member can include a channel and a chamber connected to the channel. In some embodiments, the shank can be positioned in the channel and the keel can be angularly moveable within the chamber.

In some embodiments, the chamber can have a first angular boundary and a second angular boundary, and the angular movement of the keel within the chamber can be limited by the first and second angular boundaries.

In some embodiments, the first angular boundary and the second angular boundary can define a circular sector having an angle from about 30° to about 150°.

In some embodiments, the implant assembly can further include a first limiter and a second limiter disposed on a proximal surface of the neck portion. In some embodiments, the first and second limiters can be configured to limit rotational movement of the humeral component relative to the adaptor.

In some embodiments, the first limiter can be angularly spaced apart from the second limiter from about 30° to about 150°.

In some embodiments, the first and second limiters can be connected by a curved ring.

Certain embodiments of the disclosure concern further concern an implant assembly including a humeral component, an adaptor, and a glenosphere component. The humeral component can have a stem portion and a neck portion proximal to the stem portion. The stem portion can be configured for fixation to a humerus, and the neck portion can be angularly oriented relative to the stem portion. The adaptor can be rotatably coupled to the neck portion of the humeral component around a rotational axis. The glenosphere component can have a base and a convex surface. The base can be configured for fixation to a glenoid fossa of scapula, and the convex surface can be configured to articulate against a concave surface of the adaptor. The rotational axis can form a fixed angle relative to the stem portion of the humeral component. The neck portion can further include a first limiter and a second limiter that are configured to limit rotational movement of the humeral component relative to the adaptor. The assembly can further include a locking mechanism configured to allow rotational movement of the humeral component relative to the adaptor but resist displacement of the adaptor along the rotational axis.

The foregoing and other objects, features, and advantages of the invention will become more apparent from the following detailed description, which proceeds with reference to the accompanying figures.

BRIEF DESCRIPTION OF THE DRAWINGS

FIG. 1A shows a side elevation view of an implant assembly including a humeral component and an adaptor, according to one embodiment.

FIG. 1B shows a side cross-sectional view of the implant assembly of FIG. 1A.

FIG. 3 shows a side cross-sectional view of an implant assembly including a humeral component and an adaptor having a shank extended from a geometric center of the adaptor, according to another embodiment.

FIG. 4A shows a side cross-sectional view of an implant assembly including a humeral component and an adaptor having a shank extended off the geometric center of the adaptor, according to yet another embodiment.

FIG. 4B shows the front perspective view of the implant assembly of FIG. 4A.

FIG. 7B shows the implant assembly of FIG. 7A, wherein the adaptor is coupled to the humeral component.

FIG. 7C shows a front cross-sectional view of the humeral component depicted in FIG. 7B.

FIG. 9B shows the implant assembly of FIG. 9A, wherein the adaptor is coupled to the humeral component and rotates in the counter-clockwise direction.

FIG. 9C shows the implant assembly of FIG. 9A, wherein the adaptor is coupled to the humeral component and rotates in the clockwise direction.

FIG. 10A shows another embodiment of an implant assembly comprising an adaptor and a humeral component.

FIG. 10B shows a back-side view of the adaptor depicted in FIG. 10A.

FIG. 10C shows a front view of the humeral component depicted in FIG. 10A.

DETAILED DESCRIPTION

Figure 2:
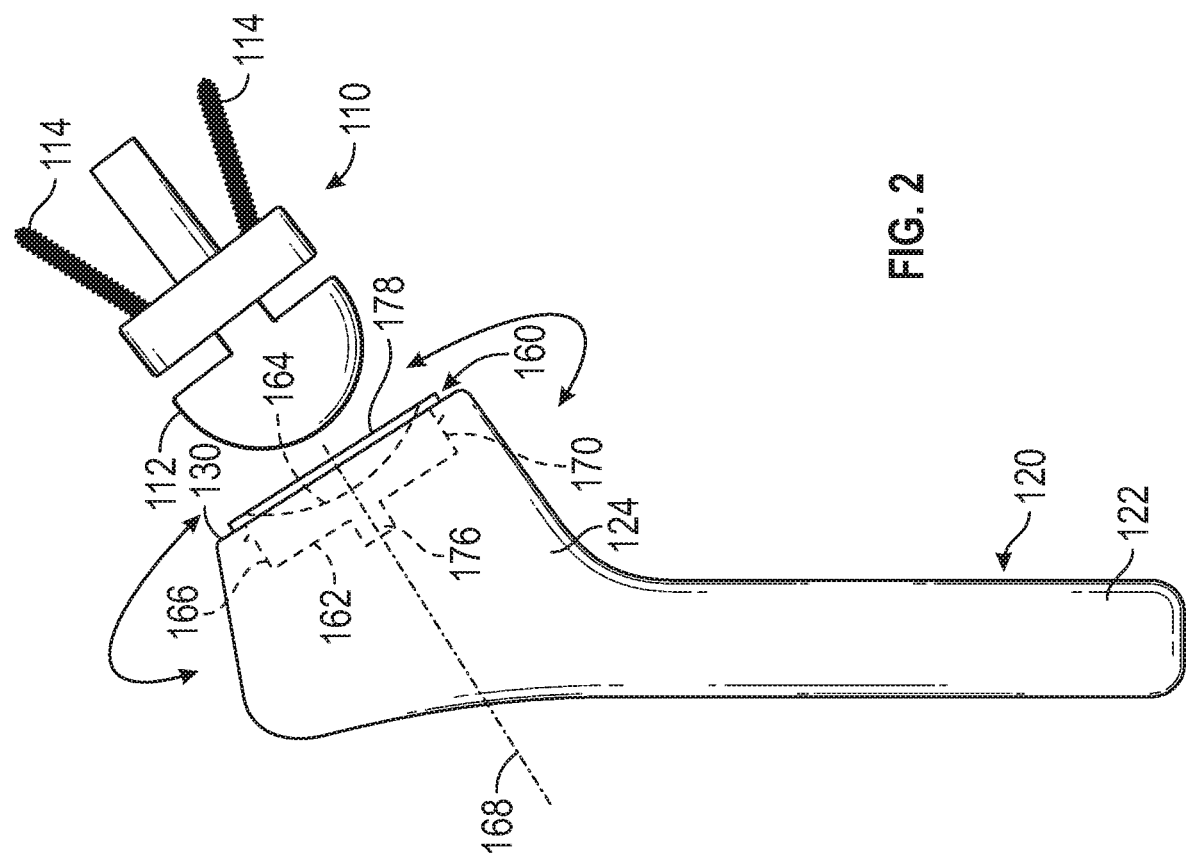
FIG. 2 shows a side elevation view of the implant assembly of FIG. 1A and a corresponding glenosphere component.
Figure 1C:
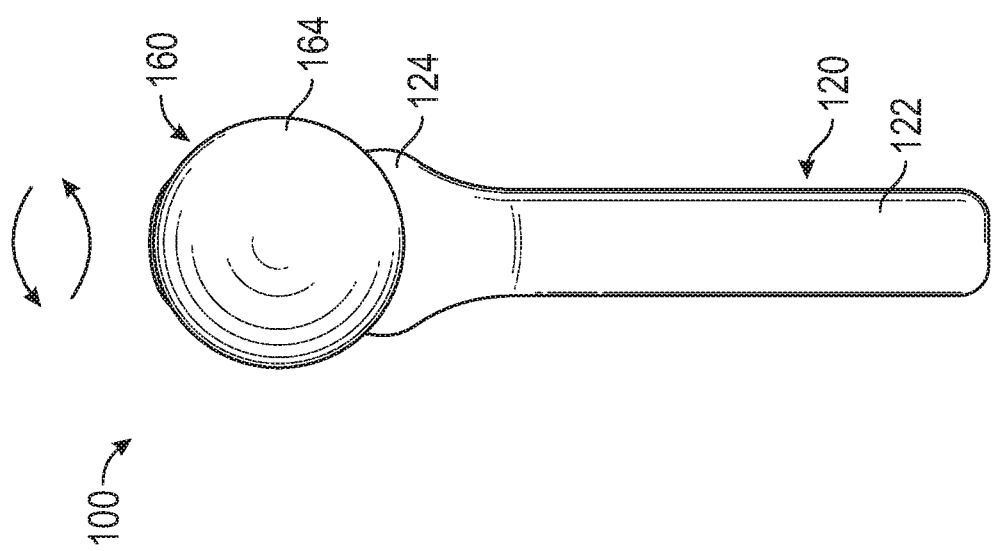
FIG. 1C shows a front view of the implant assembly of FIG. 1A.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

FIGS. 1A-1C and FIG. 2 show an exemplary implant assembly 100 for reverse shoulder arthroplasty, according to one embodiment. As shown, the implant assembly 100 includes a humeral component 120 and an adaptor 160. The humeral component 120 can have a stem portion 122 and a neck portion 124. The stem portion 122 can be configured for fixation to a humerus. The neck portion 124 can be angularly oriented relative to the stem portion 122 along a neck axis 126. For example, the neck axis 126 can form an angle θ with respect to a longitudinal axis 128 of the stem portion 122. In an exemplary embodiment, the angle θ can range from about 110 degrees to about 150 degrees. In some embodiments, the humeral component can comprise a metal material such as stainless steel or a metal alloy material such as titanium alloy, cobalt-chromium alloy, etc.

The adaptor 160 can have a first bearing surface 162 (also referred to as a "distal bearing surface") and a second bearing surface 164 (also referred to as a "proximal bearing surface") opposite the first bearing surface 162. In some embodiments, the adaptor can have a generally cylinder-shaped body 166 between the first and second bearing surfaces 162, 164.

The proximal bearing surface 164 of the adaptor 160 can be configured to interface with a glenosphere component 110 (see e.g., FIG. 2) to allow the glenosphere component 110 to articulate relative to the adaptor 160.

In the embodiment shown in FIGS. 1A-1C and FIG. 2, the proximal bearing surface 164 can be concave so as to interact with a convex surface 112 of the glenosphere component 110, which can have one or more anchoring members 114 configured for securing the glenosphere component 110 to a glenoid fossa of scapula. Thus, the proximal bearing surface 164 and the glenosphere component 110 can form and support the glenosphere-bearing articulation.

In some embodiments, the proximal bearing surface 164 can have an upper rim 178 which has a generally circular shape with a diameter ranging from about 20 mm to about 50 mm. In some embodiments, the concave proximal bearing surface 164 can have a depth from about 1 mm to about 10 mm.

In some embodiments, the proximal bearing surface 164 can comprise a material that is generally made from crosslinked polyethylene, highly crosslinked polyethylene, poly ethyl-ethyl ketone, ceramic, metal, or any other biocompatible material.

As shown in FIGS. 1A-1C and FIG. 2, the adaptor 160 can be rotatably coupled to the neck portion 124 of the humeral component 120. In the depicted embodiment, the neck portion 124 includes a receptacle 132 configured to receive the adaptor 160. The receptacle 132 can be sized and shaped to accommodate at least a lower portion 170 of the body 166 of the adaptor 160, while allowing rotational movement of the body 166 in the receptacle 132 with negligible friction. As shown in FIG. 2, at least a portion of the upper portion 172 of the body 166 can extend proximally relative to a proximal surface 130 when the lower portion 170 of the body 166 is fit into the receptacle 132. In other embodiments (not shown), the body 166 can be completely fit into the receptacle 132 such that an upper rim 178 of the body 166 is flush against the proximal surface 130.

The distal bearing surface 162 of the adaptor 160 can interface with an articulating surface 134 of the neck portion 124 to allow the humeral component 120 to rotate relative to the adaptor 160. In the depicted embodiment, the floor of the receptacle 132 serves as the articulating surface 134 of the neck portion 124.

In the embodiment depicted in FIGS. 1A-1C and FIG. 2, both the distal bearing surface 162 of the adaptor 160 and the articulating surface 130 of the neck portion 124 are flat or planar. In other embodiments (not shown), the distal bearing surface 162 and the articulating surface 130 can have curved shapes that are complimentary to each other. For example, the distal bearing surface 162 can be slightly convex and the articulating surface 130 can be slightly concave to matingly receive the distal bearing surface 162. In another example, the articulating surface 130 can be slightly convex and the distal bearing surface 162 can be slightly concave to matingly receive the articulating surface 130. The distal bearing surface 162 and the articulating surface 130 can also have other complementarily matched shapes so long as the humeral component 120 can rotate smoothly relative to the adaptor 160.

In some embodiments, the distal bearing surface 162 can comprise a material that is generally made from crosslinked polyethylene, highly crosslinked polyethylene, poly ethyl-ethyl ketone, ceramic, metal, or any other biocompatible material.

In some embodiments, the articulating surface 134 of the neck portion 124 can be configured to be smooth and highly polished so as to reduce wear of the distal bearing surface 162.

Coupling between the adaptor 160 and the neck portion 124 can be implemented by various means, for example, by matingly engaging a first coupling member positioned on the adaptor 160 with a complementarily arranged second coupling member positioned on the neck portion 124. In the embodiment depicted in FIGS. 1A-1C and FIG. 2, the first coupling member includes a shaft 176 extending outwardly from the distal bearing surface 162, and the second coupling member includes a recess 136 located underneath the articulating surface 134.

In some embodiments, the shaft 176 can have a uniform diameter ranging from about 1 mm to about 5 mm along its length, which can range from about 2 mm to about 10 mm. The recess 136 can be connected to the receptacle 132 through an opening 138 on the articulating surface 134. The recess 136 can be sized and shaped to matingly receive the shaft 176 while allowing nearly frictionless rotation of the shaft 176 therein.

In other embodiments (not shown), the relative positions of the shaft and the recess can be switched. For example, the second coupling member can include a shaft extending outwardly relative to the proximal surface 130 of the neck portion 124, and the first coupling member can include a recess in the adaptor 160 configured to receive the shaft.

As depicted, the humeral component 120 can be configured to rotate about a rotational axis 168 relative to the adaptor 160. In some embodiments, the first coupling member or the shaft 176 can be aligned or coaxial with the rotational axis 168.

In some embodiments, the rotational axis 168 can be generally perpendicular to the articulating surface 134 of the neck portion 124. Thus, the articular surface 134 can define a two-dimensional plane of rotation for the adaptor 160. In some embodiments, the articulating surface 134 can be generally parallel to the proximal surface 130 of the neck portion 124.

In some embodiments, the rotational axis 168 can be generally parallel to the neck axis 126. Thus, the rotational axis 168 can form a fixed angle relative to the longitudinal axis 128 of the stem portion 122. In some embodiments, the rotational axis 168 can be identical to the neck axis 126.

In the embodiment shown in FIGS. 1A-1C and FIG. 2, the distal bearing surface 162 rotates in a concentric manner because the rotational axis 168 passes through a geometric center 180 of the distal bearing surface 162. In other embodiments, as described more fully below, the distal bearing surface can rotate in an eccentric manner because the geometric center of the distal bearing surface can have a radial offset relative to the rotational axis 168.

In some embodiments, the implant assembly 100 can further include a locking mechanism configured to prevent the adaptor 160 from decoupling from the humeral component 120. In some embodiments, the locking mechanism can include a tongue-and-groove joint between the adaptor 160 and the humeral component 120.

For example, in the embodiment shown in FIGS. 1A-1C and FIG. 2, a circumferential tongue 182 can protrude radially outward from the body 166 of the adaptor 160, and the humeral component 120 can have a complementarily arranged, circumferential groove 140 recessed from on the peripheral wall 142 of the receptacle 132. The groove 140 can be so positioned, sized, and shaped that, when the tongue 182 is received in the groove 140, the adaptor 160 can freely rotate about the rotational axis 168 but cannot move along the rotational axis 168. In other words, the rotation of the adaptor 160 can be generally constrained in the two-dimensional plane defined by the articulating surface 134.

In other embodiments (not shown), the relative positions of the tongue and the groove can be switched. For example, a circumferential tongue can protrude radially inwardly from the peripheral wall 142 of the receptacle 132, and a circumferential groove can be complementarily arranged on the body 166 of the adaptor. Although types of locking mechanism (e.g., peripheral slots and pegs, etc.) can also be employed so long as it allows free rotational movement of the humeral component 120 relative to the adaptor 160 but resist displacement of the adaptor 160 from the plane of rotation.

Limiting the articulation between the adaptor 160 and the humeral component 120 to one plane of motion is advantageous because it allows the humeral component 120 to freely rotate even if the distal bearing surface 162 contacts a bone or soft tissue while rotating. This would allow improved internal and external rotation of a person's arm so as to allow the person to position the arm in space. Limiting the rotation to one plane of motion prevent dislocation of the humeral component 120 or of the distal bearing surface 162.

In some embodiments, the width of the groove 140 can be a little larger than the width of the tongue 182 such that the tongue 182 cannot fully occupy the groove 140. Instead, after receiving the tongue 182, the groove 140 can be left with a small gap space (e.g., about 0.5-2 mm in width), which can provide a wiggle room that allows the adaptor 160 to wobble slightly, but still limits its displacement, along the rotational axis 168.

FIG. 3 shows another embodiment of implant assembly 200 for reverse shoulder arthroplasty. The implant assembly 200 includes a humeral component 220 and an adaptor 260, which are respectively similar to the humeral component 120 and the adaptor 160 described above except that they employ different coupling and locking mechanisms.

As shown, the adaptor 260 has a first distal bearing surface 262, a proximal bearing surface 264, and a generally cylinder-shaped body 266 between the distal and proximal bearing surfaces 262, 264. In the depicted embodiment, the proximal bearing surface 264 is concave, and the distal bearing surface 262 is planar. The proximal bearing surface 264 is configured to interface with a glenosphere component 110 to allow the glenosphere component 110 to articulate relative to the adaptor 260. The distal bearing surface 262 is configured to interface with an articulating surface 234 on the neck portion 224 of the humeral component 220 to allow the humeral component 220 to rotate about a rotational axis 268 relative to the adaptor 260.

In the embodiment depicted in FIG. 3, the adaptor 260 can be coupled to the humeral component 220 by matingly engaging a shank 276 of the adaptor 260 with a corresponding channel 236 positioned on the neck portion 224.

The shank 276, which extends outwardly from the distal bearing surface 262, can have a non-uniform diameter along its length. In some embodiments, the diameter of the shank 276 can vary from about 5 mm to about 20 mm, and the length of the shank 276 can range from about 2 mm to about 20 mm.

In some embodiments, the shank 276 can be an integrated component of the adaptor 260. In other embodiments, the shank 276 can be detachably coupled to the adaptor 260. For example, a proximal end of the shank 276 can be inserted into a slot on the adaptor 260 to form an interference fit.

In some embodiments, the shank 276 can comprise a metal or alloy material to improve the strength of the shank 276 and enhance the stability of the distal bearing surface 262.

The articulating surface 234 can be a planar surface within a receptacle 232 on the neck portion 224. The channel 236 can be positioned underneath the articulating surface 234 and form a part of the receptacle 232. The receptacle 232 can be configured to accommodate at least a portion of the body 266 of the adaptor 260, while allowing rotational movement of the body 266 in the receptacle 232 with negligible friction.

In the embodiment depicted in FIG. 3, the rotational axis 268 coincides with the longitudinal axis of the shank 276 and the channel 236, and passes through the geometric center 280 of the distal bearing surface 262. Accordingly, the distal bearing surface 262 can rotate about the rotational axis 268 in a concentric manner.

Similarly, the implant assembly 200 can further include a locking mechanism configured to prevent the adaptor 260 from decoupling from the humeral component 220. As depicted in FIG. 3, the locking mechanism can include two separate tongue-and-groove joints. A first tongue-and-groove joint can be formed by a circumferential tongue 240 protruding radially inwardly from the peripheral wall 242 of the receptacle 232 and a circumferential groove 282 complementarily arranged on the body 266 of the adaptor 260. A second tongue-and-groove joint can be formed by a circumferential tongue 244 protruding radially inwardly from the peripheral wall 246 of the channel 236 and a circumferential groove 284 complementarily arranged on the shank 276.

Although specific locking mechanism is shown in FIG. 3 for illustrative purposes, it should be understood that any type of locking mechanism can be employed so long as it allows free rotational movement of the humeral component 220 relative to the adaptor 260 but resists displacement of the adaptor 260 along the rotational axis 268. For example, for each tongue-and-groove joint, the relative positions of the tongue and the groove can be switched. In addition, any number of tongue-and-groove joints can be employed.

Figure 5:
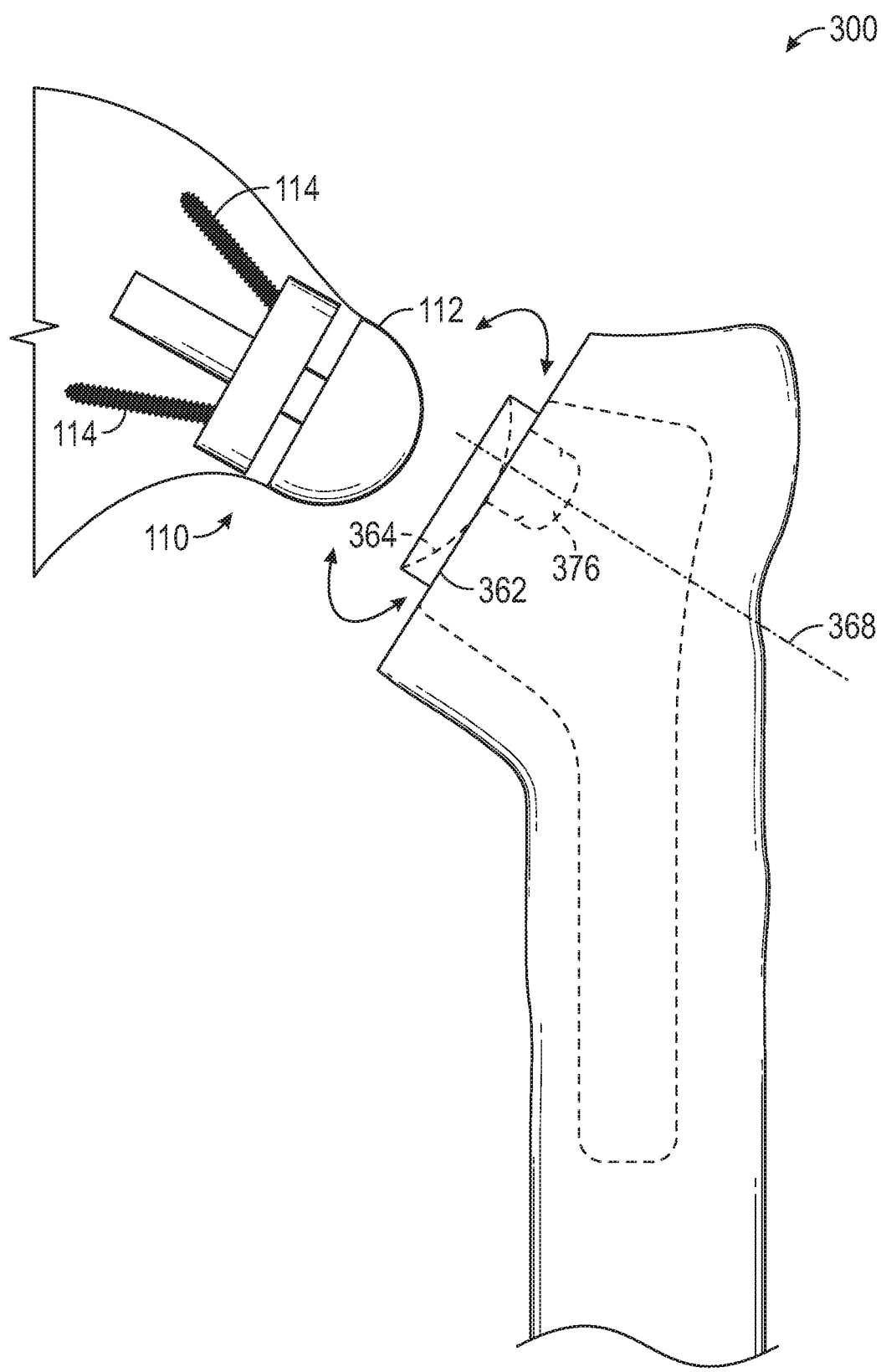
FIG. 5 shows a side elevation view of the implant assembly of FIG. 4A being placed in a humerus and a corresponding glenosphere component.
Figure 6A:
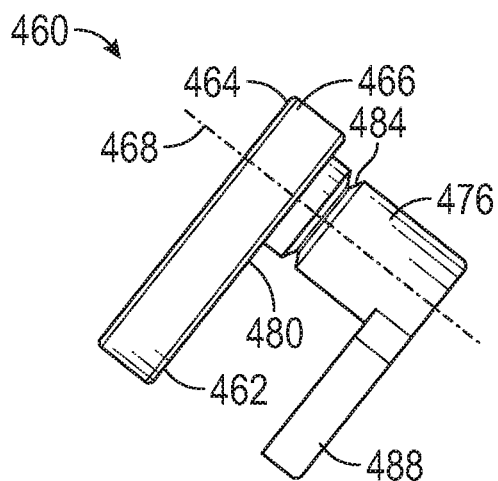
FIG. 6A shows a side elevation view of an adaptor, according to another embodiment.
Figure 6B:
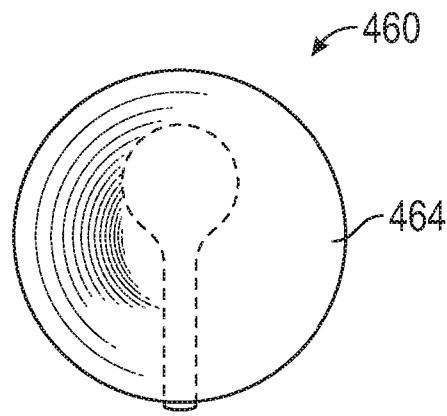
FIG. 6B shows a front view of the adaptor of FIG. 6A.
Figure 6C:
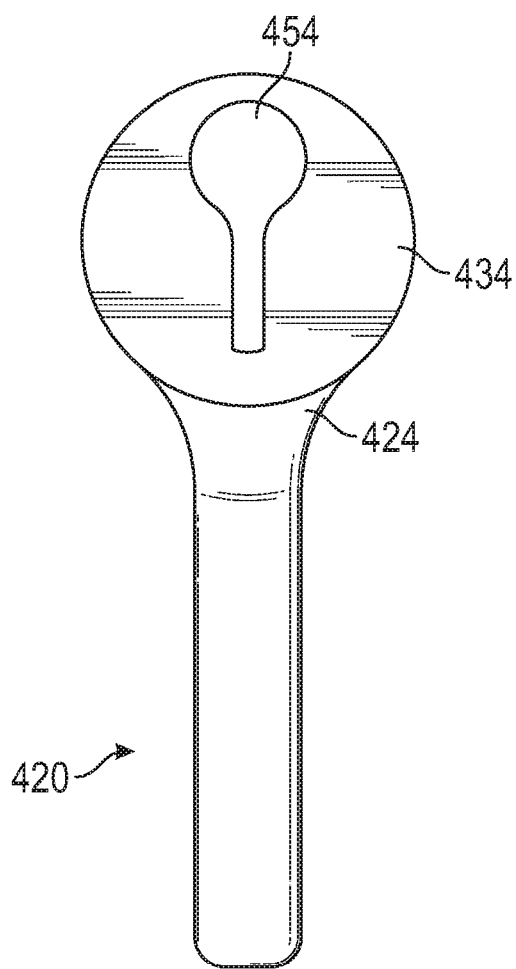
FIG. 6C shows a front view of a humeral component, according to another embodiment.
Figure 6D:
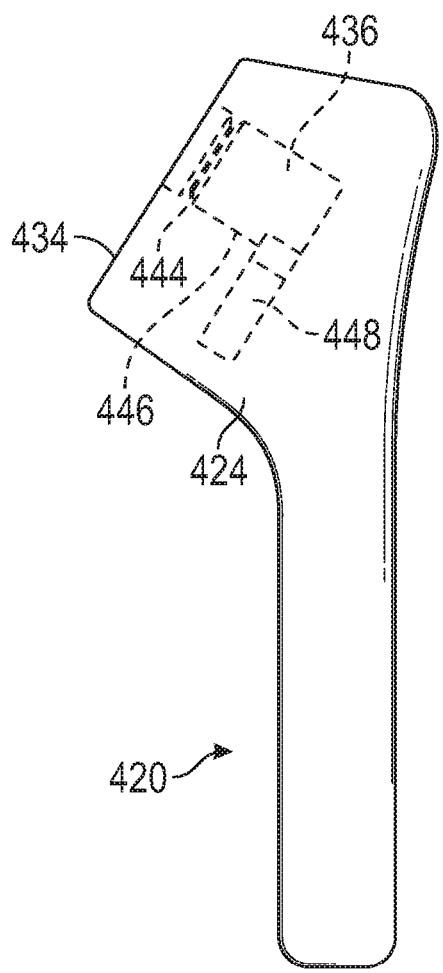
FIG. 6D shows a side elevation view of the humeral component of FIG. 6C.
Figure 7A:
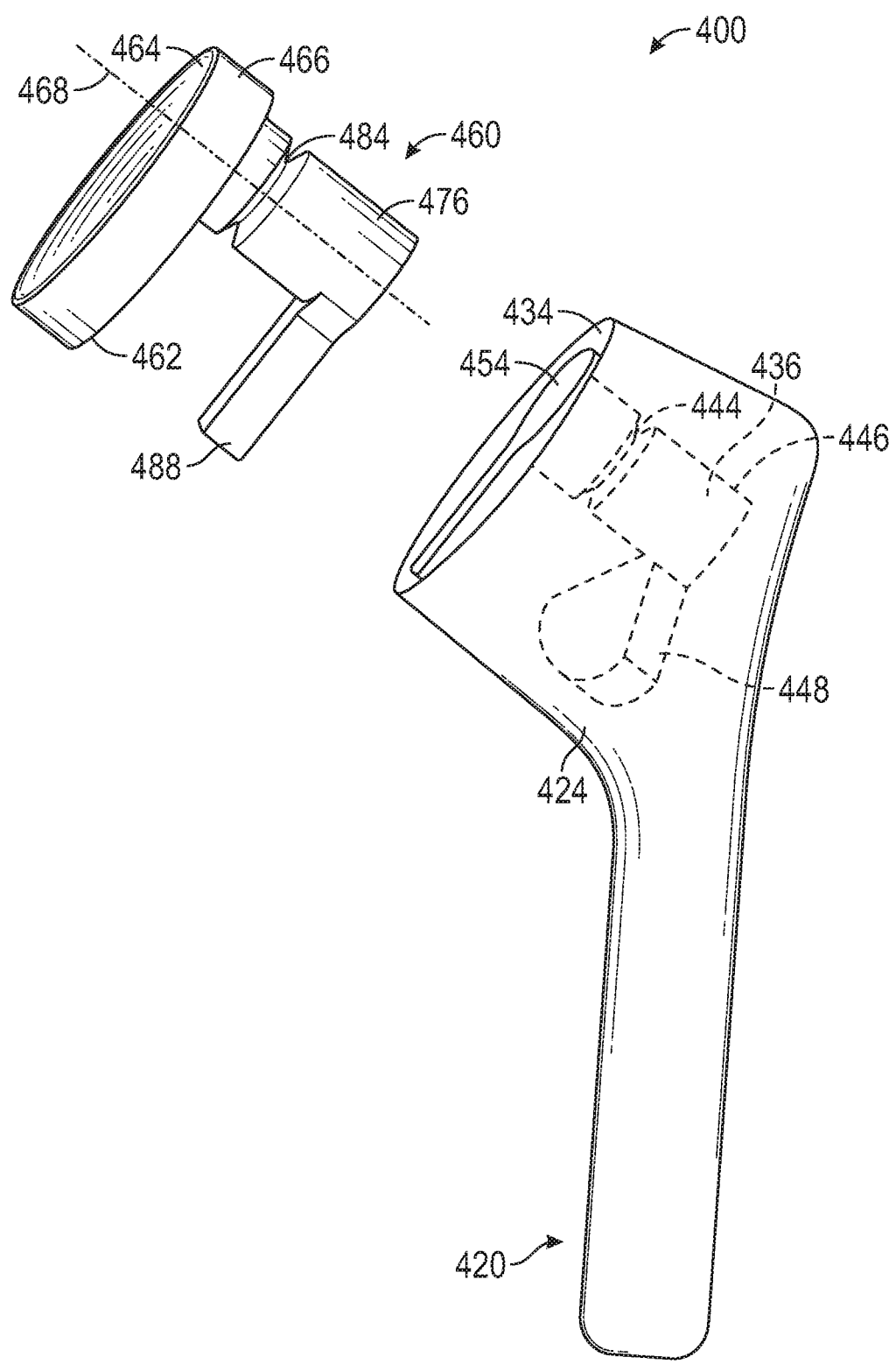
FIG. 7A shows a side perspective view of an implant assembly including the adaptor depicted in FIG. 6A and the humeral component depicted in FIG. 6C, wherein the adaptor and the humeral component are separate from each other.
Figure 8A:
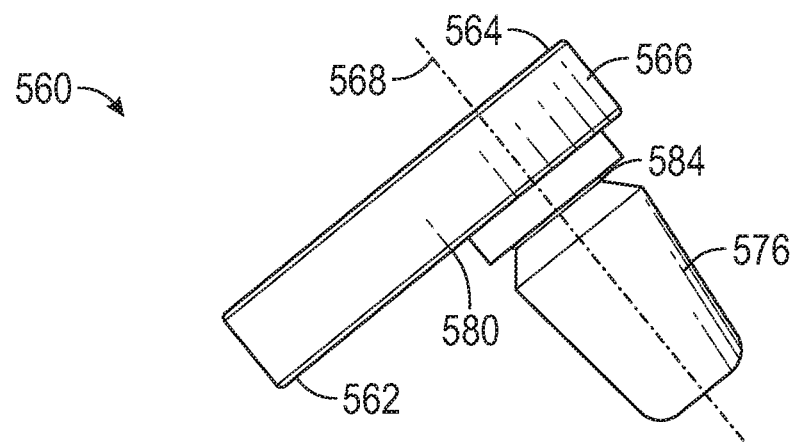
FIG. 8A shows a side elevation view of an adaptor, according to yet another embodiment.
Figure 8B:
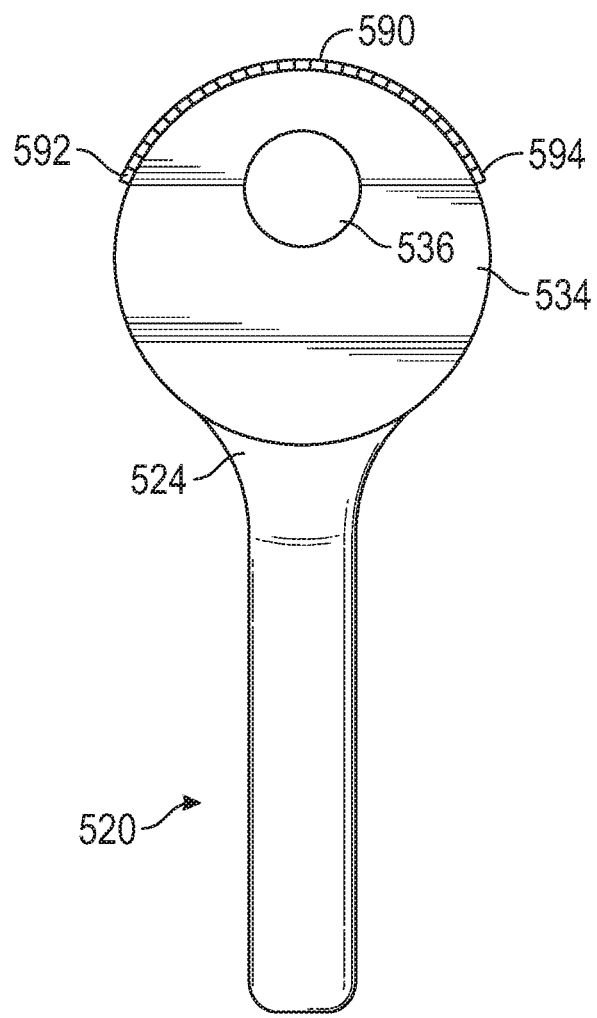
FIG. 8B shows a front view of a humeral component, according to yet another embodiment.
Figure 9A:
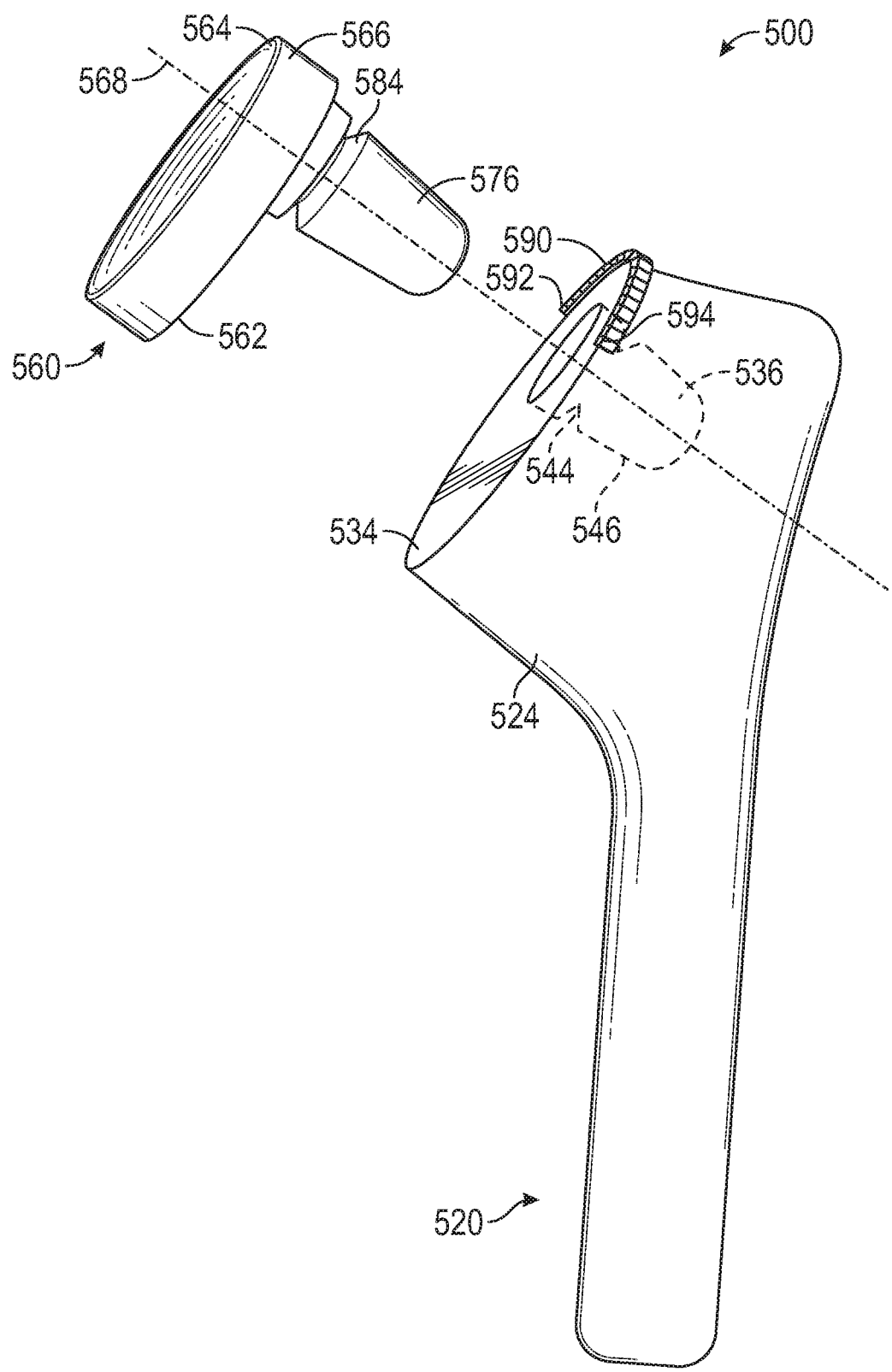
FIG. 9A shows a side perspective view of an implant assembly including the adaptor depicted in FIG. 8A and the humeral component depicted in FIG. 8B, wherein the adaptor and the humeral component are separate from each other.

FIGS. 4A-4B and FIG. 5 show another embodiment of implant assembly 300 for reverse shoulder arthroplasty. The implant assembly 300 includes a humeral component 320 and an adaptor 360, which are respectively similar to the humeral component 220 and the adaptor 260 described above except that they employ a different shank design that allows eccentric rotation of the adaptor 360.

As shown, the adaptor 360 has a first distal bearing surface 362, a proximal bearing surface 364, and a generally cylinder-shaped body 366 between the distal and proximal bearing surfaces 362, 364. In the depicted embodiment, the proximal bearing surface 364 is concave, and the distal bearing surface 362 is planar. The proximal bearing surface 364 is configured to interface with the glenosphere component 110 to allow the glenosphere component 110 to articulate relative to the adaptor 360. The distal bearing surface 362 is configured to interface with an articulating surface 334 on the neck portion 324 of the humeral component 320 to allow the humeral component 320 to rotate about a rotational axis 368 relative to the adaptor 360.

As shown in FIGS. 4A and 5, the adaptor 360 can be coupled to the humeral component 320 by matingly engaging a shank 376 of the adaptor 360 with a corresponding channel 336 positioned on the neck portion 324. In the depicted embodiment, the articulating surface 334 is the proximal surface of the neck portion 324, and the channel 336 is positioned underneath the articulating surface 334. Thus, the entire body 366 of the adaptor 360 is disposed proximal to the articulating surface 334 when the shank 376 is engaged with the channel 336.

Similarly, the implant assembly 300 can include a locking mechanism configured to prevent the adaptor 360 from decoupling from the humeral component 320. As shown, the locking mechanism can include a tongue-and-groove joint formed by a circumferential tongue 344 protruding radially inwardly from the peripheral wall 346 of the channel 336 and a circumferential groove 384 complementarily arranged on the shank 376.

In the depicted embodiment, the shank 376 has a generally cylindrical shape and extends outwardly from the distal bearing surface 362. The diameter of the shank 376 can be generally uniform along its length, ranging from about 5 mm to about 20 mm. In other embodiments, the diameter of the shank 376 can vary along its length. The length of the shank 376 can range from about 2 mm to about 20 mm.

In some embodiments, the shank 376 can be an integrated component of the adaptor 360. In other embodiments, the shank 376 can be detachably coupled to the adaptor 360.

In some embodiments, the shank 376 can comprise a metal or alloy material to improve the strength of the shank 376 and enhance the stability of the distal bearing surface 362.

In the depicted embodiment, the shank 376 is offset from the center of rotation of the adaptor 360 to allow eccentric rotation of the humeral component 320 relative to the adaptor 360. Specifically, the rotational axis 368 coincides with the longitudinal axis of the shank 376 and the channel 336. The geometric center 380 of the distal bearing surface 362 has a radial offset r1 relative to the rotational axis 368 because the longitudinal axis of the shank 376 intersects with the distal bearing surface 362 at a location 386 away from the geometric center 380.

Thus, as illustrated in FIG. 4B, the distal bearing surface 362 can rotate in an eccentric manner such that the adaptor 360 can rotate (in clockwise or counter-clockwise direction) slightly sideway of the articulating surface 334 of the neck portion 324. Such eccentric center of rotation of the distal bearing surface 362 allows more mobility of the humeral component 320 relative to the adaptor 360.

FIGS. 6A-6D and FIGS. 7A-7C show another embodiment of implant assembly 400 for reverse shoulder arthroplasty. The implant assembly 400 includes a humeral component 420 and an adaptor 460, which are respectively similar to the humeral component 320 and the adaptor 360 described above except that they employ a different shank design that limits the angular motion of the adaptor 460.

As shown, the adaptor 460 has a first distal bearing surface 462, a proximal bearing surface 464, and a generally cylinder-shaped body 466 between the distal and proximal bearing surfaces 462, 464. In the depicted embodiment, the proximal bearing surface 464 is concave, and the distal bearing surface 462 is planar. The proximal bearing surface 464 is configured to interface with the glenosphere component 110 to allow the glenosphere component 110 to articulate relative to the adaptor 460. The distal bearing surface 462 is configured to interface with an articulating surface 434 on the neck portion 424 of the humeral component 420 to allow the humeral component 420 to rotate about a rotational axis 468 relative to the adaptor 460.

The adaptor 460 can be coupled to the humeral component 420 by matingly engaging a shank 476 of the adaptor 460 with a corresponding channel 436 positioned on the neck portion 424. In the depicted embodiment, the articulating surface 434 is the proximal surface of the neck portion 424, and the channel 436 is positioned underneath the articulating surface 434. Thus, the entire body 466 of the adaptor 460 is disposed proximal to the articulating surface 434 when the shank 476 is engaged with the channel 436.

Similarly, the implant assembly 400 can include a locking mechanism configured to prevent the adaptor 460 from decoupling from the humeral component 420. As shown, the locking mechanism can include a tongue-and-groove joint formed by a circumferential tongue 444 protruding radially inwardly from the peripheral wall 446 of the channel 436 and a circumferential groove 484 complementarily arranged on the shank 476.

In the depicted embodiment, the shank 476 extends outwardly from the distal bearing surface 462. The diameter of the shank 476 can range from about 5 mm to about 20 mm, and the length of the shank 476 can range from about 2 mm to about 20 mm.

In some embodiments, the shank 476 can be an integrated component of the adaptor 460. In other embodiments, the shank 476 can be detachably coupled to the adaptor 460.

In some embodiments, the shank 476 can comprise a metal or alloy material to improve the strength of the shank 476 and enhance the stability of the distal bearing surface 462.

The geometric center 480 of the distal bearing surface 462 has a radial offset relative to the rotational axis 468 which coincides with the longitudinal axis of the shank 476 and the channel 436. Thus, the distal bearing surface 462 can rotate in an eccentric manner such that the adaptor 460 can rotate slightly sideway of the articulating surface 434.

Unlike the embodiments described above, rotation of the humeral component 420 relative to the adaptor 460 is restrained within a limited angular range. Specifically, the implant assembly 400 includes a paddle-like keel 488 angularly extending from the shank 476 and an open area or chamber 448 connected to the channel 436. The chamber 448 is complementarily arranged with respect to the keel 488 such that the keel 488 can be angularly moveable within the chamber 448.

As shown in FIG. 7C, the chamber 448 can have a first angular boundary 450 and a second angular boundary 452. Thus, the angular movement of the keel 488 within the chamber 448 can be limited by the first and second angular boundaries 450, 452, which can prevent excessive rotation of the humeral component 420 relative to the adaptor 460. In other words, the boundaries 450 and 452 can function as two rotation limiters that limit the rotational movement of the humeral component 420 relative to the adaptor 460.

In some embodiments, the first angular boundary 450 and the second angular boundary 452 can define a circular sector having an angle from about 30° to about 150°. In particular embodiments, the angle of the circular sector can range from about 60° to about 120°.

In the depicted embodiment, the keel 488 is connected to the distal end portion of the shank 476 and generally forms a right angle with the shank 476. In other embodiments (not shown), the keel can be connected to a different portion of the shank (e.g., the keel may be connected to the shank at a position that is proximal relative to the tongue-and-groove joint), and/or the keel may not be perpendicular to the shank.

In the depicted embodiment, the keel 488 is integrated with the shank 476 such that they form a unitary piece. The proximal surface or articulating surface 434 of the neck portion 424 has a slotted or keyhole type of opening 454 which allows insertion of the shank 476 and the keel 488 into the channel 436 and the chamber 448, respectively. In alternative embodiments, the keel 488 can be a separate piece which can be detachably coupled to the shank 476. Thus, after inserting the shank 476 into the channel 436, the keel 488 can be inserted into the chamber 448 through a side slot (not shown) on the neck portion 424 and coupled to the shank 476.

Although the keel-in-chamber structure is described with respect to specific embodiment shown in FIGS. 6A-6D and FIGS. 7A-7C, it should be understood that the same structural components can be incorporated in other embodiments, for example, the embodiments depicted in FIGS. 1A-1C and FIGS. 2-3, to limit the concentric rotation of humeral component relative to the adaptor within a predefined angular range.

FIGS. 8A-8B and FIGS. 9A-9C show yet another embodiment of implant assembly 500 for reverse shoulder arthroplasty. The implant assembly 500 includes a humeral component 520 and an adaptor 560, which are respectively similar to the humeral component 420 and the adaptor 460 described above except that a different mechanism is employed to limit the angular motion of the adaptor 560.

As shown, the adaptor 560 has a first distal bearing surface 562, a proximal bearing surface 564, and a generally cylinder-shaped body 566 between the distal and proximal bearing surfaces 562, 564. In the depicted embodiment, the proximal bearing surface 364 is concave, and the distal bearing surface 562 is planar. The proximal bearing surface 564 is configured to interface with the glenosphere component 110 to allow the glenosphere component 110 to articulate relative to the adaptor 560. The distal bearing surface 562 is configured to interface with an articulating surface 534 on the neck portion 524 of the humeral component 520 to allow the humeral component 520 to rotate about a rotational axis 568 relative to the adaptor 560.

The adaptor 560 can be coupled to the humeral component 520 by matingly engaging a shank 576 of the adaptor 560 with a corresponding channel 536 positioned on the neck portion 524. In the depicted embodiment, the articulating surface 534 is the proximal surface of the neck portion 524, and the channel 536 is positioned underneath the articulating surface 534. Thus, the entire body 566 of the adaptor 560 is disposed proximal to the articulating surface 534 when the shank 576 is engaged with the channel 536.

Similarly, the implant assembly 500 can include a locking mechanism configured to prevent the adaptor 560 from decoupling from the humeral component 520. As shown, the locking mechanism can include a tongue-and-groove joint formed by a circumferential tongue 544 protruding radially inwardly from the peripheral wall 546 of the channel 536 and a circumferential groove 584 complementarily arranged on the shank 576.

In the depicted embodiment, the shank 576 extends outwardly from the distal bearing surface 562. The diameter of the shank 576 can range from about 5 mm to about 20 mm, and the length of the shank 576 can range from about 2 mm to about 20 mm.

In some embodiments, the shank 576 can be an integrated component of the adaptor 560. In other embodiments, the shank 576 can be detachably coupled to the adaptor 560.

In some embodiments, the shank 576 can comprise a metal or alloy material to improve the strength of the shank 576 and enhance the stability of the distal bearing surface 562.

The geometric center 580 of the distal bearing surface 562 has a radial offset relative to the rotational axis 568 which coincides with the longitudinal axis of the shank 576 and the channel 536. Thus, the distal bearing surface 562 can rotate in an eccentric manner such that the adaptor 560 can rotate slightly sideway of the articulating surface 534.

Similarly, rotation of the humeral component 520 relative to the adaptor 560 is restrained within a limited angular range. However, instead of using a keel-in-chamber structure, a different restraining mechanism is employed. As shown, the humeral component 520 can have a curved ring 590 protruding outwardly from the periphery of the articulating surface 534. The curved ring 590 has a first end 592 and a second end 594, both of which can limit the eccentric rotation of the humeral component 520 relative to the adaptor 560. For example, eccentric rotation of the humeral component 520 relative to the adaptor 560 in the counter-clockwise direction can be limited by the first end 592 (see, e.g., FIG. 9B), whereas eccentric rotation of the humeral component 520 relative to the adaptor 560 in the clockwise direction can be limited by the second end 594 (see, e.g., FIG. 9C).

In some embodiments, the first end 592 can be angularly spaced apart from the second end 594 from about 30° to about 150°. In particular embodiments, the angle between the first end 592 and the second end 594 can range from about 60° to about 120°.

In other embodiments (not shown), rotation of the humeral component 520 relative to the adaptor 560 can be restrained by two unconnected, stem-like limiters that are respectively disposed at the locations corresponding to the first and second ends 392, 394, protruding outwardly from the articulating surface 534.

Although the curved ring or unconnected limiters are described with respect to specific embodiment shown in FIGS. 8A-8B and FIGS. 9A-9C, similar structural components can be incorporated in other embodiments, for example, the embodiments depicted in FIGS. 1A-1C and FIGS. 2-3, to limit the concentric rotation of humeral component relative to the adaptor within a predefined angular range.

FIGS. 10A-10C show another embodiment of an implant assembly 600 comprising an adaptor 660 and a humeral component 620. Similar to the implant assembly depicted in FIGS. 4A-4B, the implant assembly 600 is configured to allow eccentric rotation of the humeral component 620 relative to the adaptor 660.

As shown, the adaptor 660 has a first distal bearing surface 662, a proximal bearing surface 664, and a generally cylinder-shaped body 666 between the distal and proximal bearing surfaces 662, 664. The proximal bearing surface 664 can be concave, and the distal bearing surface 662 can be planar. The proximal bearing surface 664 can be configured to interface with the glenosphere component (not shown) to allow the glenosphere component to articulate relative to the adaptor 660. The distal bearing surface 662 can be configured to interface with an articulating surface 634 on the neck portion 624 of the humeral component 620 to allow the humeral component 620 to rotate about a rotational axis 668 relative to the adaptor 660.

The adaptor 660 can be coupled to the humeral component 620 by matingly engaging a shank 676 of the adaptor 660 with a corresponding channel 636 positioned on the neck portion 624. In the depicted embodiment, the articulating surface 634 is the proximal surface of the neck portion 624, and the channel 636 is positioned underneath the articulating surface 634. Thus, the entire body 666 of the adaptor 660 can be disposed proximal to the articulating surface 634 when the shank 676 is engaged with the channel 636.

Similarly, the implant assembly 600 can include a locking mechanism configured to prevent the adaptor 660 from decoupling from the humeral component 620. For example, the locking mechanism can include a tongue-and-groove joint formed by a circumferential groove 644 on the peripheral wall of the channel 636 and a circumferential tongue 684 extending outwardly and complementarily arranged on the shank 676.

As shown, the shank 676 can be offset from the center of rotation of the adaptor 660. Specifically, the rotational axis 668 coincides with the longitudinal axis of the shank 676 and the channel 636. The geometric center 680 of the distal bearing surface 662 has a radial offset r2 relative to the rotational axis 668 because the longitudinal axis of the shank 676 intersects with the distal bearing surface 662 at a location spaced away from the geometric center 680.

Thus, the distal bearing surface 662 can rotate in an eccentric manner such that the adaptor 660 can rotate (in clockwise or counter-clockwise direction) slightly sideway of the articulating surface 634 of the neck portion 624, thus allowing more mobility of the humeral component 620 relative to the adaptor 660. Although not shown, it should be understood that in alternative embodiments, the implant assembly 600 can also be configured to allow concentric rotation of humeral component relative to the adaptor.

In addition, the implant assembly 600 can be configured to limit the angular motion of the humeral component 620 relative to the adaptor 660. For example, the implant assembly 600 can have a rotation-limiting mechanism that includes a first rotation control member located on the adaptor 660 and a second rotation control member located on the neck portion 624, wherein the first and second rotation control members can engage with each other to limit the rotation of the humeral component 620 relative to the adaptor 660. In some embodiments, the first and second rotation control members can form a tab-in-groove configuration where a tab is configured to be received in and moveable within a corresponding groove.

For example, the rotation-limiting mechanism can include a curved groove 690 located on the distal bearing surface 662 of the adaptor 660 and a tab 696 extending outwardly from the articulating surface 634 of the neck portion 624. The tab 696 can be so positioned and sized that when the adaptor 660 is coupled to the humeral component 620, the tab 696 can be received in the groove 690.

The groove 690 has a first end 692 and a second end 694 which can function as two rotation limiters. For example, the angular movement of the tab 696 within the groove 690 can be limited by the first and second ends 692, 694, which can prevent excessive rotation of the humeral component 620 relative to the adaptor 660.

In some embodiments, the first and second ends 692, 694 of the groove 690 can be configured to have rounded shape. In some embodiments, the tap 696 can have rounded edges. The rounded ends of the groove 690 and/or the rounded edges of the tap 696 can be advantageous to prevent polyethylene damage when rotation of the humeral component 620 relative to the adaptor 660 causes the tab 696 to interface with the first or second end of the groove 690.

In some embodiments, the first end 692 can be angularly spaced apart from the second end 694 from about 30° to about 150°. In particular embodiments, the angle between the first end 692 and the second end 694 can range from about 60° to about 120°.

In some embodiments, the groove 690 can have an arc length from about 1 cm to about 3 cm. In some embodiments, the groove 690 can have a width from about 1 mm to about 4 mm. In some embodiments, the groove 690 can have a depth from about 1 mm to about 10 mm.

In some embodiments, the tab 696 can have a curved shape. In some embodiments, the tab 696 can have a width from about 1 mm to about 4 mm. In some embodiments, the tab 696 can have a height from about 1 mm to about 10 mm. In some embodiments, the tab 696 can have a curved length from about 5 mm to about 80 mm. In some embodiments, the articular surface 634 can have a generally circular shape with a diameter from about 2 cm to about 5 cm.

In alternative embodiments, the relative positions of the groove and tab can be switched for the rotation-limiting mechanism. For example (not shown), the rotation-limiting mechanism can include a curved groove located on the articulating surface of the neck portion and a tab extending outwardly from the distal bearing surface of the adaptor, wherein the tab can be so positioned and sized that when the adaptor is coupled to the humeral component, the tab can be received in the groove.

It should be understood that the disclosed embodiments can be adapted to deliver and implant prosthetic devices in orthopedic surgical procedures other than should arthroplasty, such as hip arthroplasty, knee arthroplasty, elbow arthroplasty, ankle arthroplasty, etc.

As used herein, with reference to the adaptor and the humeral component, "proximal" refers to a position, direction, or portion of a device that is closer to the glenoid fossa of scapula, while "distal" refers to a position, direction, or portion of a device that is further away from the glenoid fossa of scapula. The terms "longitudinal" and "axial" refer to an axis extending in the proximal and distal directions, unless otherwise expressly defined.

As used in this application and in the claims, the singular forms "a," "an," and "the" include the plural forms unless the context clearly dictates otherwise. Additionally, the term "includes" means "comprises." Further, the terms "coupled" and "connected" generally mean physically, mechanically, chemically, magnetically, and/or electrically linked and do not exclude the presence of intermediate elements between the coupled or connected items absent specific contrary language.

Directions and other relative references (e.g., inner, outer, etc.) may be used to facilitate discussion of the drawings and principles herein, but are not intended to be limiting. For example, certain terms may be used such as "inside," "outside,", "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. As used herein, "and/or" means "and" or "or", as well as "and" and "or".

In view of the many possible embodiments to which the principles of the disclosure may be applied, it should be recognized that the illustrated embodiments are only examples and should not be taken as limiting the scope of the claimed subject matter. Rather, the scope of the claimed subject matter is defined by the following claims and their equivalents.

The invention claimed is:

1. An implant assembly for reverse shoulder arthroplasty, the assembly comprising:
    a humeral component having a stem portion and a neck portion, the stem portion being configured for fixation to a humerus of a patient, and the neck portion being angularly oriented relative to the stem portion; and
    an adaptor coupled to the humeral component, the adaptor having a first bearing surface and a second bearing surface opposite the first bearing surface;
    wherein the first bearing surface of the adaptor interfaces with an articulating surface of the neck portion to allow the humeral component to rotate relative to the adaptor about a rotational axis of the adaptor;
    wherein the adaptor and the humeral component form a locking mechanism that prevents the adaptor from decoupling from the humeral component while allowing the humeral component to remain rotatable relative to the adaptor after the implant assembly is implanted in the patient; and
    wherein the second bearing surface of the adaptor is configured to interface with a glenosphere component to allow the glenosphere component to articulate relative to the adaptor.

2. The implant assembly of claim 1, wherein the adaptor comprises a first coupling member matingly engaged with a second coupling member of the neck portion.

3. The implant assembly of claim 2, wherein the first coupling member comprises a shaft extending from the first bearing surface, and the second coupling member comprises a recess in the neck portion configured to receive the shaft.

4. The implant assembly of claim 2, wherein the first and the second coupling members are aligned with the rotational axis of the adaptor.

5. The implant assembly of claim 4, wherein the rotational axis passes through a geometric center of the first bearing surface.

6. The implant assembly of claim 4, wherein a geometric center of the first bearing surface has a radial offset relative to the rotational axis.

7. The implant assembly of claim 2, wherein the locking mechanism comprises a tongue-and-groove joint between the adaptor and the humeral component so as to allow rotational movement of the humeral component relative to the adaptor but resist displacement of the adaptor from the plane of rotation.

8. The implant assembly of claim 2 wherein the first coupling member comprises a shank member extending outwardly from the first bearing surface and a keel member angularly extending from the shank member.

9. The implant assembly of claim 8, wherein the second coupling member comprises a channel and a chamber connected to the channel, wherein the shank is positioned in the channel and the keel is angularly moveable within the chamber.

10. The implant assembly of claim 9, wherein the chamber has a first angular boundary and a second angular boundary, and the angular movement of the keel within the chamber is limited by the first and second angular boundaries.

11. The implant assembly of claim 10, wherein the first angular boundary and the second angular boundary defines a circular sector having an angle from about 30° to about 150°.

12. The implant assembly of claim 2, further comprising a first limiter and a second limiter, the first and second limiters being configured to limit rotational movement of the humeral component relative to the adaptor.

13. The implant assembly of claim 12, wherein the first limiter is angularly spaced apart from the second limiter from about 30° to about 150° with respect to the rotational axis of the adaptor.

14. The implant assembly of claim 12, wherein the first and second limiters are disposed on a proximal surface of the neck portion.

15. The implant assembly of claim 12, further comprising a curved groove located on the first bearing surface of the adaptor and a tab extending outwardly from the articulating surface of the neck portion, the tab being configured to be received in and moveable within the curved groove, wherein a first and second ends of the groove define the respective first and second limiters.

16. The implant assembly of claim 1, further comprising the glenosphere component, wherein the glenosphere component comprises a base configured for fixation to a glenoid fossa of scapula and a convex surface that articulates against the second bearing surface of the adaptor, wherein the second bearing surface is concave.

17. The implant assembly of claim 1, wherein the first bearing surface of the adaptor is planar.

18. The implant assembly of claim 1, wherein the first bearing surface of the adaptor is curved.

19. An implant assembly for reverse shoulder arthroplasty, the assembly comprising:
    a humeral component having a stem portion and a neck portion proximal to the stem portion, the stem portion being configured for fixation to a humerus, and the neck portion is angularly oriented relative to the stem portion; and an adaptor rotatably coupled to the neck portion of the humeral component such that the adaptor rotates relative to the neck portion about a rotational axis;

wherein the rotational axis forms a fixed angle relative to the stem portion of the humeral component; and wherein the adaptor remains rotatable relative to the humeral component after the implant assembly is implanted in the patient.

20. An implant assembly for reverse shoulder arthroplasty, the assembly comprising:

a humeral component having a stem portion and a neck portion proximal to the stem portion, the stem portion being configured for fixation to a humerus, and the neck portion is angularly oriented relative to the stem portion;

an adaptor rotatably coupled to the neck portion of the humeral component such that the adaptor rotates relative to the neck portion about a rotational axis; and a glenosphere component having a base and a convex surface, the base configured for fixation to a glenoid fossa of scapula, and the convex surface configured to articulate against a concave surface of the adaptor wherein the rotational axis forms a fixed angle relative to the stem portion of the humeral component;

wherein the neck portion further comprises a first limiter and a second limiter that are configured to limit rotational movement of the humeral component relative to the adaptor;

wherein the assembly further comprises a locking mechanism configured to allow rotational movement of the humeral component relative to the adaptor but resist displacement of the adaptor along the rotational axis; and wherein the humeral component remains rotatable relative to the adaptor after the implant assembly is implanted in the patient.

\* \* \* \* \*